United States Patent [19]

Cohen

[11] Patent Number: 5,269,301
[45] Date of Patent: Dec. 14, 1993

[54] MULTIMODE SYSTEM FOR MONITORING AND TREATING A MALFUNCTIONING HEART

[75] Inventor: Todd J. Cohen, Port Washington, N.Y.

[73] Assignee: Leonard Bloom, Towson, Md.; a part interest

[21] Appl. No.: 963,113

[22] Filed: Oct. 19, 1992

Related U.S. Application Data

[63] Continuation-in-part of Ser. No. 699,472, May 13, 1991, Pat. No. 5,156,148, which is a continuation-in-part of Ser. No. 416,024, Oct. 2, 1989, Pat. No. 5,014,698, which is a continuation-in-part of Ser. No. 385,544, Jul. 27, 1989, Pat. No. 4,984,572, which is a continuation of Ser. No. 233,367, Aug. 18, 1988, Pat. No. 4,967,749, which is a continuation-in-part of Ser. No. 105,030, Oct. 6, 1987, Pat. No. 4,774,950.

[51] Int. Cl.$^5$ .................................... A61N 1/36
[52] U.S. Cl. ........................................ 607/6; 607/18; 607/25; 604/66
[58] Field of Search ............. 128/419 PG, 419 D, 697, 128/709, 419 P

[56] References Cited

U.S. PATENT DOCUMENTS

| 4,785,812 | 11/1988 | Pihl et al. | 128/419 D |
| 4,870,341 | 9/1989 | Pihl et al. | 128/419 D |
| 5,097,830 | 3/1992 | Eikefjord et al. | 128/419 D |

Primary Examiner—Kyle L. Howell
Assistant Examiner—George Manuel
Attorney, Agent, or Firm—Leonard Bloom

[57] ABSTRACT

A system for monitoring a patient and treating the malfunctioning heart of the patient, either in an automatic mode or in a semiautomatic mode, includes means which derive at least one electrical signal resulting from action of the patient's heart and means which derive at least one physiologic signal from or related to the patient's circulatory system. A central processing unit, which may be a programmable microprocessor, with a RAM and a ROM, receives and responds to the at least one electrical signal and to the at least one physiologic signal. Output means, which may include a heart assist pump, pacers, drug delivery devices and cardioverting-/-defibrillating apparatuses, controlled by the central processing unit provides corrective measure(s) to the patient. Adjustable or variable baselines, against which a representation of the current, short-term magnitude of the selected physiologic parameter or parameters are provided. The variable baseline(s) is (are) a representation of the selected physiologic parameter(s) determined over a long term of greater duration than the short term over which the current magnitude(s) of the parameter(s) is (are) measured. In its monitoring only mode, the system monitors vital signs and/or the like, including the above-mentioned electrical signal and the physiologic signal and displays them on a monitor.

43 Claims, 14 Drawing Sheets

MULTIMODE SYSTEM FOR MONITORING AND TREATING A MALFUNCTIONING HEART

CROSS REFERENCE TO RELATED APPLICATION

This application is a continuation-in-part of copending application Ser. No. 699,472 of Todd J. Cohen filed May 13, 1991 and entitled "System for Treating a Malfunctioning Heart" now U.S. Pat. No. 5,156,148. The Ser. No. 699,472 application is a continuation-in-part of application Ser. No. 416,024 of Todd J. Cohen filed Oct. 2, 1989 and entitled "Method of and System for Monitoring and Treating a Malfunctioning Heart", which has matured as U.S. Pat. No. 5,014,698 granted May 14, 1991. The Ser. No. 416,024 application, in turn, is a continuation-in-part of application Ser. No. 385,544, which has matured as U.S. Pat. No. 4,984,572 granted Jan. 15, 1991, of Todd J. Cohen filed Jul. 27, 1989 and entitled "Hemodynamically Responsive System for and Method of Treating a Malfunctioning Heart" which is a continuation of Ser. No. 233,367, which has matured as U.S. Pat. No. 4,967,749 issued Nov. 6, 1990, of Todd J.Cohen filed Aug. 18, 1988 and entitled "Hemodynamically Responsive System for and Method of Treating a Malfunctioning Heart" which is a continuation-in-part of Ser. No. 105,030 of Todd J. Cohen filed on Oct. 6, 1987 and entitled "Hemodynamically Responsive System for and Method of Treating a Malfunctioning Heart", which has matured as U.S. Pat. No. 4,774,950 granted Oct. 4, 1988. The disclosures of the prior applications are incorporated herein in their entirety respectively by reference.

BACKGROUND OF THE INVENTION

1. Field of the Invention

This invention relates to a system for treating a malfunctioning heart which also has a monitoring capability. The invention provides for the cardioverting/defibrillation of a malfunctioning heart, as well as the possibility of overcoming a tachycardia and bradycardia manifestations without resorting to either cardioverting or defibrillating the heart. The invention also may involve identifying and treating asystole, ischemia, early infarction and heart failure, to name a few other representative disorders sought to be treated.

2. Description of the Prior Art

In recent years, substantial progress has been made in pacemakers and in the development of cardioverting-/defibrillating techniques for effectively treating various heart disorders and arrhythmias. Past efforts have resulted in the development of implantable electronic pacemakers and standby cardiovertersdefibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping below a fixed predetermined level and not returning above the predetermined level for a given period of time.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a predetermined minimum threshold), on the other hand.

Still further, research in this area has resulted in the development of a heart rate detector system which accurately measures heart rate from a variety of different electrocardiogram (ECG) signal shapes, one such system is disclosed in U.S. Pat. No. 4,393,877 of Imran et al.

The U.S. Pat. No. 4,770,177 of Schroeopel discloses a pacer which paces a heart in accordance with the heart-/pacer rate needed to produce a required cardiac output while a person is exercising or undergoes emotional stress in response to changes in venous blood vessel diameter. The pacer is adapted to be implanted in a human body and has a pulse generator and control circuitry, which may be realized by a microprocessor. A pacing lead adapted to be implanted in a heart has a tip electrode adapted to engage and supply pacing pulses to a right ventricle of a heart. A piezoelectric sensor determines changes in a diameter of a vein in the human body. Computing circuitry, including the control circuitry, relates the changes in venous blood vessel diameter with the required pacing rate needed to supply a desired cardiac output, and causes the pacer to pace the heart at the required rate when the heart is not naturally paced. The pacer of Schroeppel is not combined with any cardioverter/defibrillator.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used antitachycardia device is the automatic implantable cardioverter-defibrillators which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. This cardioverter-defibrillator has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al.,, "Recent Clinical Experience with the Automatic Implantable Cardioverter-Defibrillator, *Medical Instrumentation*, Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", *JACC*, Vol. 6, No. 2, pages 461-466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski to al., supra, and the Mirowski, supra publications set out, in summary form, background material relating to the defibrillating/cardioverting arts against which the present invention was made to correct the ischemia (in a closed-loop fashion). Closed loop intravenous drug delivery systems have been developed (and are undergoing evaluation) for the treatment of heart failure. Such systems could be incorporated into an implantable device to permit the delivery of electrical therapy (pacing/cardioversion/defibrillation) as well as drug therapy, to correct a malfunctioning heart.

In addition to the standard automatic cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One drawback with many current systems is that they function in a single mode; that is, such systems apply therapy, such as cardioverting/defibrillating pulses to the myocardium automatically, without waiting for confirmation or intervention by medical personnel.

External patient monitoring systems have been proposed. Some are commercially available. An exemplary patient monitoring system, which may be used in an operating room, a cardiac care unit and the like is disclosed in U.S. Pat. No. 4,356,486 of Mount. As disclosed, the system provides for inputting ECG waveforms, pulse data, patient temperature data, blood pressure data form separate points to derive systolic and diastolic pressures at the respective points. While not specifically disclosed, other parameters, such as respiration data (rate) could be derived as well. Such monitoring systems provide no active treatment.

A number of devices and apparatuses have been known or proposed for monitoring blood pressure and/or heart rate and the like. As general background prior art, such apparatuses and devices are disclosed in U.S. Pat. Nos. 3,087,488; 3,776,221; 4,190,886; 4,245,648; 4,252,127; 43,347,851; 4,404,974; 4,378,807; and 4,625,277.

SUMMARY OF THE INVENTION

The principle object of the present invention is to provide a multimode system for monitoring or automatically treating a patient having a malfunctioning heart or semi-automatically treating a patient having a malfunctioning heart and which provides for determining the presence of a malfunction.

A further object of the present invention is to provide a multimode system for monitoring a patient and for treating, in either a semiautomatic mode or an automatic mode, the malfunctioning heart of the patient, the system being responsive to change in at least one physiologic parameter, such as pressure(s) at one or more sites in the circulatory system of a patient, and to an electrical signal or signals derived from action of the heart.

As used herein, the term physiologic parameter means any parameter which is derived from the human body which relates information and reflects the hemodynamic state or condition of the patient. This term includes information which may be derived from a biosensor (or biosensors) or a characteristic of an electrical signal other than rate which relates hemodynamic information. An example would be the determination of ST signal changes from the electrical signal as a physiologic parameter which indicates ischemia.

The system of the present invention may incorporate a multiplicity of signals derived from physiological parameters and electrical signals derived from heart action which are processed, via a microprocessor, in selecting the treatment therapy. It is particularly geared towards the treatment of heart rhythm disturbances in an emergency room or critical care unit. The electrical signal may be the ECG from which at least heart rate is determined in a simple exemplary embodiment. The separate physiologic signal may be derived which is representative of blood pressure in the simple exemplary embodiment. A microprocessor is arranged to receive respective digital signal representations of the physiologic parameter signal(s) and the electrical signal(s) derived from heart action. The microprocessor determines if the heart rate is extremely fast, it will then look and see if there is a drop in blood pressure from the baseline modality and, if a drop in blood pressure is noted, the system will then promptly shock the patient if it is operating in its automatic mode. In the semiautomatic mode the system should signal a clinician or physician who is present and ask for confirmation. The clinician or physician would then press a button to defibrillate, if his subjective judgement is that such therapy is desirable. If on the other hand, a rapid heart rate is noted, but there is no drop in blood pressure, the patient would then be in a state of physiologic stability and would be monitored via the system. If on the other hand, the heart rate was low or below the normal range (less than 60 beats per minute) and there was no change in blood pressure, the system would simply monitor the patient's heart rhythm. If on the other hand the heart rate was low (let's say less than 60) and the blood pressure had dropped significantly, then external pacing through the standard skin patches, anterior and posterior, would then be the likely treatment and this would be prompted by the lighting of a light which would say pace on the front of the external monitoring and treatment system. The system, which could be used for bedside monitoring or monitoring via telemetry, provides an automatic treatment mode, a semiautomatic mode using external pacing or internal pacing, external defibrillation or internal defibrillation and vital signs monitoring as well as the potential of drug therapy delivery.

From one vantage point, the invention can be seen as being a multimode system for treating a patient having a malfunctioning heart in either an automatic mode or a semiautomatic mode (requiring confirmation by a clinician or physician), a third mode of operation being provided simply to monitor the patient. Means derive at least one electrical signal representative of electrical action of the patient's heart. Other means derive at least one physiologic signal from or related to the patient's circulatory system, that is, a physiologic parameter. A central processing unit, which may be a microprocessor, with its associated RAM and ROM is provided. Means input the at least one electrical signal and the at least one physiologic signal to the central processing unit. Output means controlled by the central processing unit provide a corrective measure or measures to the patient. In preferred embodiments, the central processing unit may effect a determination of both a long-term level and a current, short-term level for the selected physiological parameter and a comparison of one to the other.

The system may include means for monitoring heart rhythm to develop the at least one electrical signal, and respectively and/or in various combinations means responsive to the at least one electrical signal and to at least one signal representing a physiologic parameter for identifying stable SVT, unstable SVTI stable VT, unstable VT, stable atrial fibrillation, unstable atrial fibrillation, ventricular fibrillation, asystole, stable bradycardia, unstable bradycardia, ischemia, early infarction and heart failure alone. The central processing unit may effect a determination of both a long-term level and a current, short-term level for the selected physiological parameter and a comparison of one to the other.

In practicing the present invention ischemia may be detected by comparing short-term changes in the ST segment of the ECG to long-term (or baseline) ST segment. The time response of the physiologic signal together with the behavior of the ECG signal could indicate the presence and degree of heart failure as well as myocardial infarction. These features, together with heart rhythm control system provide a basis method for treating a malfunctioning heart selectively in an automatic or semiautomatic mode, while monitoring, the system also having a monitoring only mode.

The novel features that are considered characteristic of the invention are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

DETAILED DESCRIPTION OF THE PREFERRED EMBODIMENTS

Figure 1:
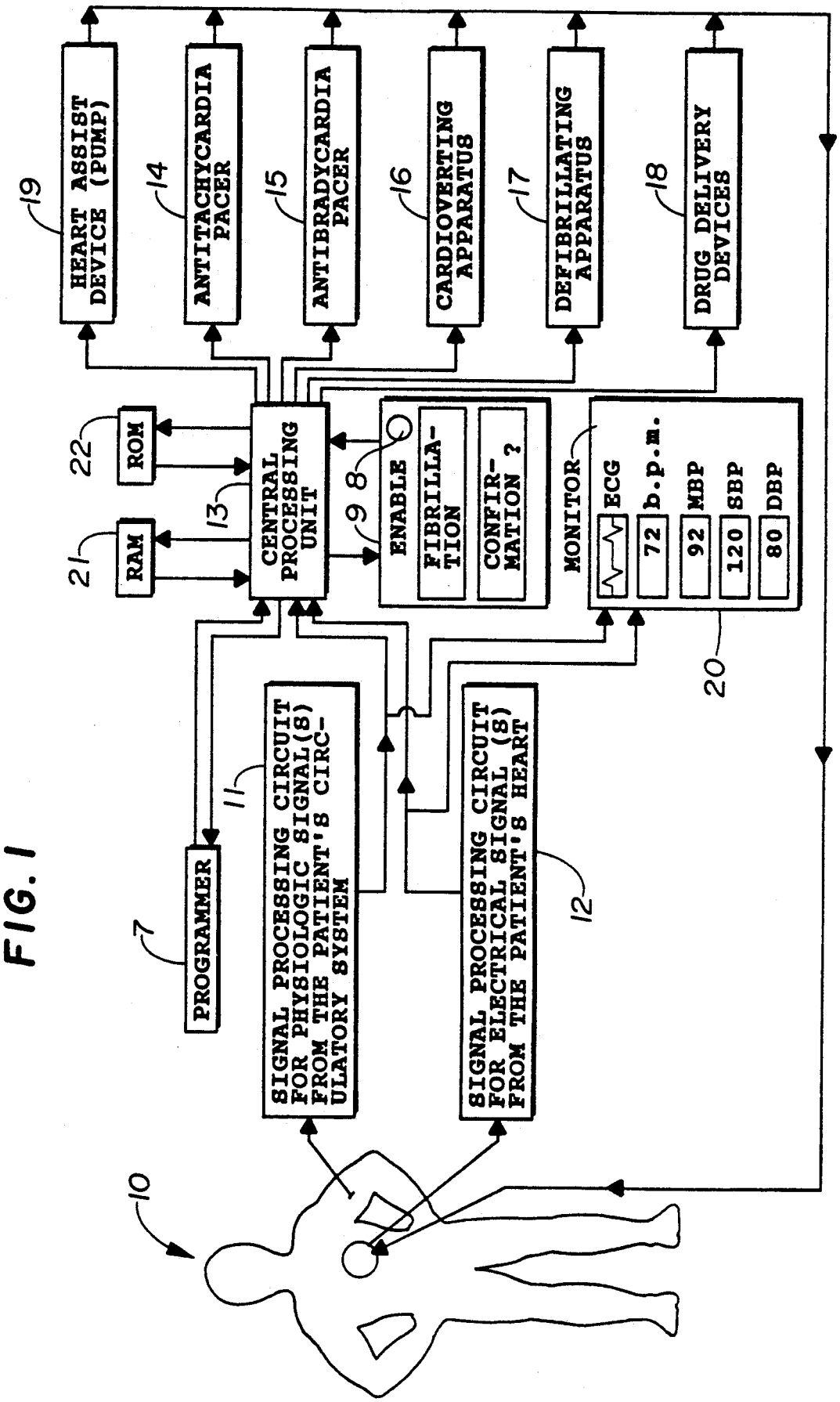
FIG. 1 is a block, generalized illustration of an exemplary, first embodiment of an electrical- and physiologic- signal responsive system for monitoring a patient and for treating a malfunctioning heart selectively and alternatively in automatic and semiautomatic modes, in accordance with the present invention.

As illustrated in FIG. 1, an exemplary system for a patient 10 includes a signal processing circuit 11 which receives signals representing a physiologic condition, such as blood pressure, at one or more sites within or related to the circulatory system of a patient. The signal(s) representing the physiologic condition(s) preferably involve hemodynamic parameter(s) at the site(s) and reflect the dynamic nature of the pressure(s) at the site(s). The system also includes a signal processing circuit 12 which receives an electrical signal or signals representing electrical action of the heart of a patient; for example, the circuit 12 may receive an electrical signal or signals obtained by conventional external EKG electrodes and which are processed to derive a signal representing the QRS complex, the R-wave (the beating rate of the heart), a signal or signals related to atrial contractions (or the like) and/or a signal or signals related to ventricular contractions (or the like).

The signals from the signal processing circuits 11 and 12 are coupled to a central processing unit 13, which may be realized by a programmable microprocessor, with an associated ROM 22 and a RAM 21. The program can be modified by using a programmer 7.

Preferably, the system illustrated in FIG. 1 includes a monitor 20, which may provide a visual and/or audible readout to aid medical personnel providing treatment for the patient. As illustrated the monitor 20 is operative to display an ECG, heart beating rate (b.p.m.), mean blood pressure (MBP), systolic blood pressure (SBP) and diastolic blood pressure (DBP). It is to be understood additional parameters may be sensed and displayed, as well. Among these parameters are $O_2$ saturation, body temperature, blood temperature, respiration rate, $K^+$ ion concentration cardiac output and impedance, to name a few. The monitor 20, as is known, may also effect recording, on strip graphs or the like, of the signals fed to the central processing unit 13, as well as the command signals from the central processing unit, which it generates in response to the physiologic signal(s) and the electrical signal(s) supplied thereto.

The central processing unit 13 provides a number of output command signals, depending on decisions made by the central processing unit 13, under control of its associated RAM 21 and ROM 22. Of course, the central processing unit 13 may elect, without producing any output command signals, to continue monitoring the electrical signal(s) and the physiologic signal(s) from the signal processing circuits 11 and 12, in the event no malfunction of the heart of the patient 10 has been identified. The signal(s) from the signal processing circuit 13 may be processed by the central processing unit 13 to derive varying, long-term baseline(s) for the physiologic parameter(s) against which current, short-term magnitude(s) of the physiologic parameter(s) is (are) to be compared. In another embodiment, the programmable central processing unit 13, in conjunction with its associated RAM 21 and ROM 22, may develop a fixed baseline or baselines, which is or are adjustable and against which the selected physiologic parameter or parameters may be compared.

In the event a malfunction of the heart of the patient 10 is identified by the central processing unit 13, the central processing unit may supply an enabling command signal or signals, depending on the nature of the identified malfunction, to one or another or more than one malfunction correcting means, illustrated as an antitachycardia pacer 14, an antibradycardia pacer 15, a cardioverting apparatus 16, a defibrillating apparatus 17, drug delivery devices 18, and a heart-assist device 19, which may be an assist pump or a similar device. It is to be appreciated that cardioverter and defibrillator may share components and be constructed as illustrated in U.S. Pat. No. 4,774,950. In its automatic mode, the central processing unit supplies the enabling command signal or signals, solely under the control of the central processing unit 13, having been programmed by the programmer 7 to operate in this particular mode. If desired, the clinician or physician under whose care the patient 10 may be, may elect to require his confirmation before the selected treatment is effected. In this case, the person in charge, using the programmer 7, would reprogram (or modify) the program so that confirmation is required. In this case, the person in charge, having the data available to him from the display 20 and a diagnosis display 9, which receives data from the central processing unit 13 and displays, in visual form, the diagnosis (illustrated in a simplified manner as "FIBRILLATION"). The diagnosis display 9 also preferably has a visual panel which flashes "CONFIRMATION?" once a diagnosis has been made, thus alerting the attending clinician or physician that the treatment is not being currently delivered and requires his or her approval or confirmation before the system delivers the proposed heart-malfunction-corrective input to the patient. If the clinician or physician agrees with the proposed treatment and diagnosis, he or she would simply press a confirmation (enable) button 8 causing the diagnosis display 9 to signal the central processing unit 13 to enable one or another or more than one of the malfunction correcting circuits 14–17.

The malfunction correcting circuits 14–17 produce respective malfunction correcting electrical output signals, which are delivered to the patient 10 as required. The drug delivery devices 18 which may consist of a number of pumps or other drug delivery devices, such as gravity operated delivery systems supply medications to the patient 10 in an effort to overcome or correct the malfunction. The heart-assist device 19, which may be a pump, when energized, aids a patient by assisting pumping action thereby reducing load on the heart or drugs which are supplied to the patient 10 in an effort to overcome the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Figure 2:
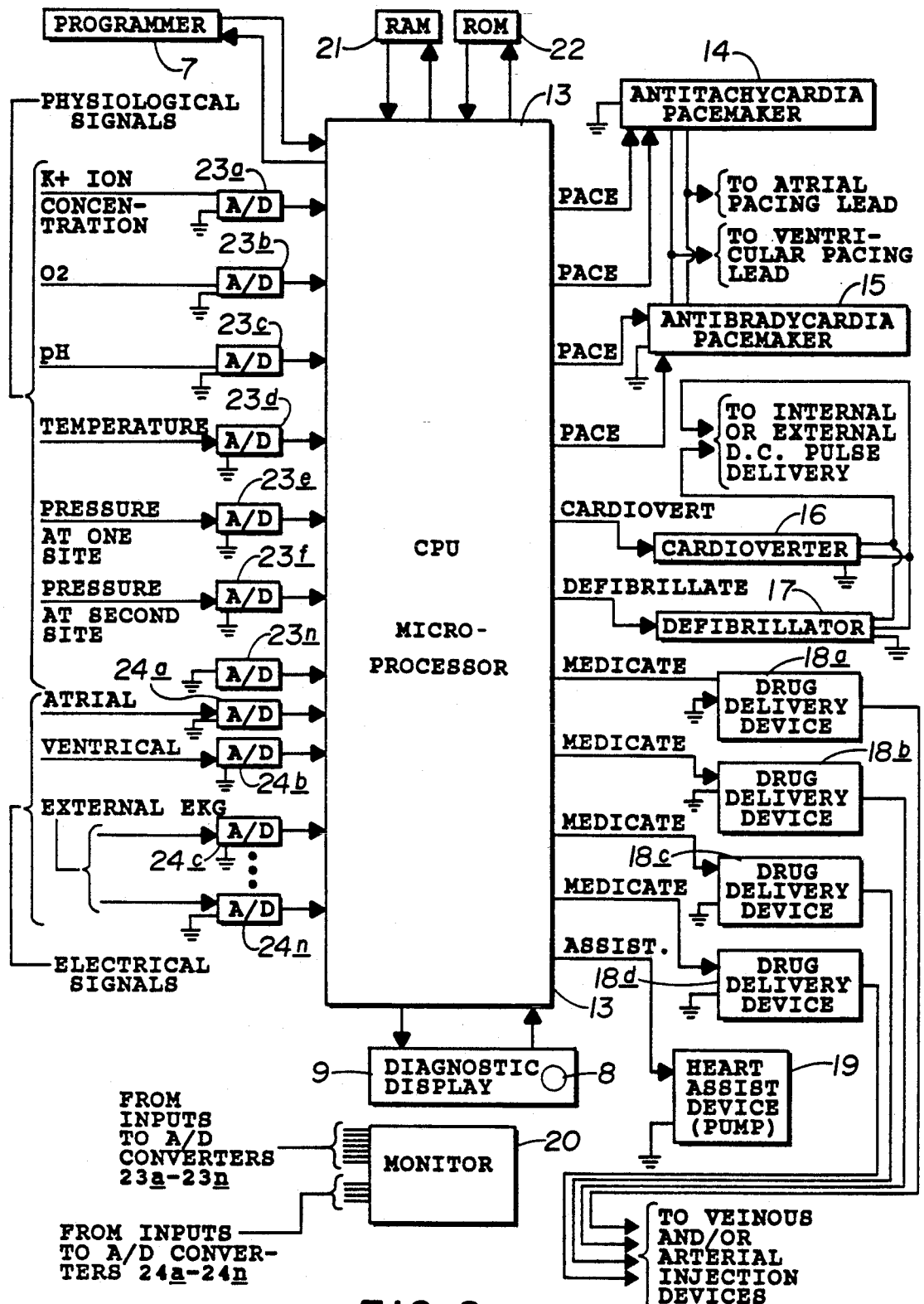
FIG. 2 is a more detailed illustration of the exemplary system shown in FIG. 1 for monitoring and treating a malfunctioning heart.

As illustrated in FIG. 2, the preferred detailed embodiment, like the more generalized illustration thereof shown in FIG. 1, is provided with a CPU 13 and its associated RAM 21 and ROM 22. The CPU 13 and its associated RAM 21 and ROM 22 constitute a computer means programmable by the programmer 7.

The input side of the system, includes a plurality of physiologic signals, actually electric analogue signal representations of physiologic conditions, shown by way of example as $K^+$ion concentration in blood, $O_2$ level in mixed venous blood or the like, pH of blood, body or blood temperature, pressure at one site in the circulatory system of the patient and pressure at another site in the circulatory system of the patient, other possible signals could represent $CO_2$ level in blood, end tidal $CO_2$ level in blood, DP/dt, cardiac output, impedance, respiratory rate and lactic acidosis, to name a few. The respective physiologic signals are converted into digital signals by respective analogue-to-digital converters 23a to 23n and supplied as distinct inputs to the CPU 13. The respective analogue physiologic signals are also fed to the monitor 20 which, like the monitor 20 (FIG. 1) may display the inputs so that the attending clinician or physician may have this data readily available to him or her.

The system of FIG. 2 includes electrical signals derived from action of the patient's heart. The electrical signals, as illustrated, include an atrial signal, a ventricular signal and a plurality of EKG signals, which are obtained by conventional means. The respective electrical signals are fed to respective analog-to-digital converters 24a–24n and are converted into respective digital signals which are fed, as distinct inputs, to the CPU 13. The signal inputs to the A/D converters 24a–24n are also fed to the monitor 20 which, like the monitor 20 (FIG. 1) may display all or a selected one or more of the inputs.

The CPU 13 effects a comparison of one or more of the digital signal representations of the physiologic signals against a fixed (for example, as disclosed in U.S. Pat. No. 4,967,749) or a varying baseline (for example, as disclosed in U.S. Pat. No. 4,774,950) representations thereof, possibly after processing the signals into signals representing mean, systolic, diastolic, pulse pressures or the like. The CPU 13 also determines the pulse rate, Rewave, QRS complex (possibly against a "template" of the patient's QRS complex when the heart is functioning properly) and/or another morphologic basis, tachycardia acceleration, atrial-ventricular timing, ST segment analysis and the like.

Figure 3:
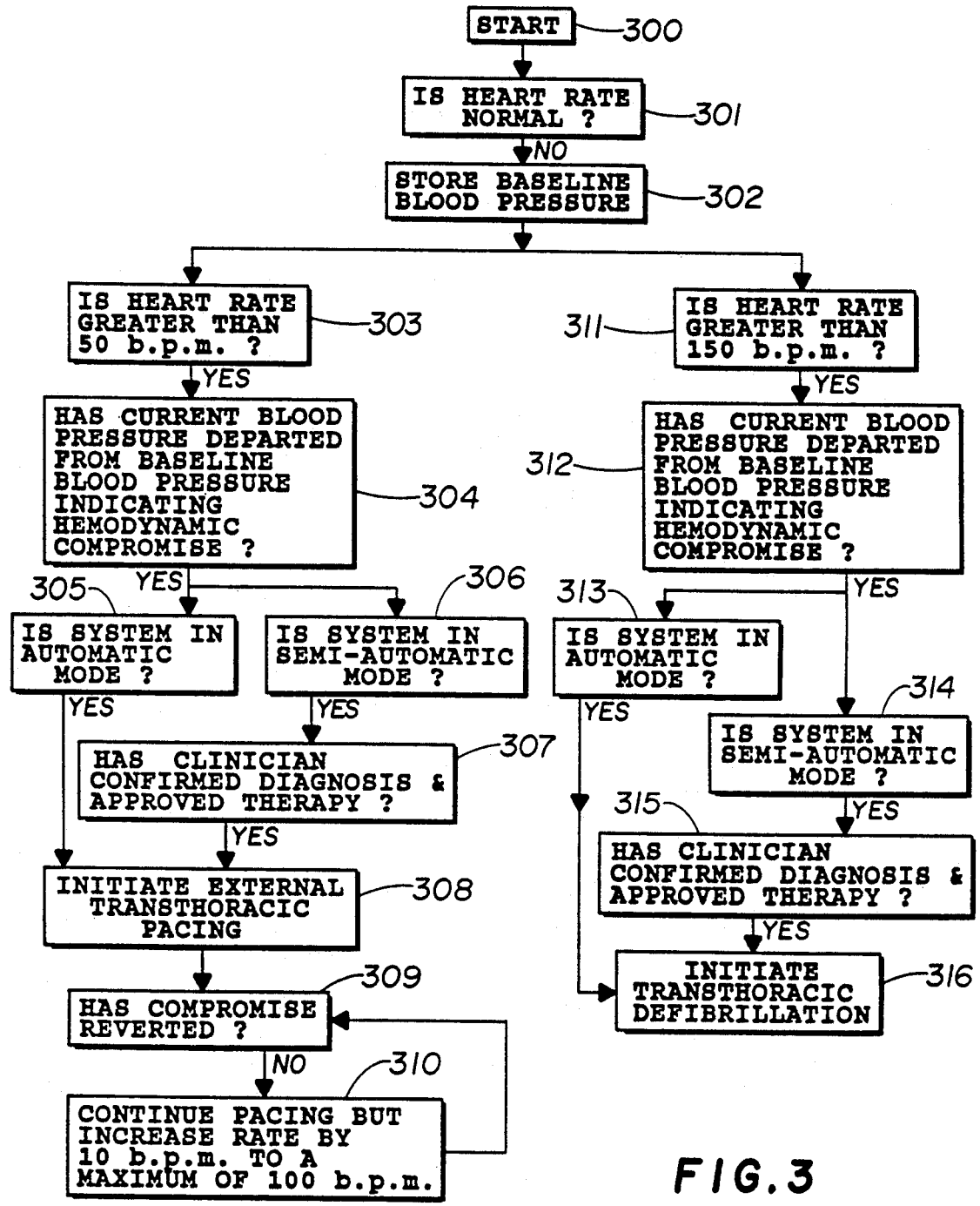
FIG. 3 constitutes a flowchart of steps which may be executed by the systems illustrated in FIGS. 1 and 2 in accordance with the present invention.
Figure 4:
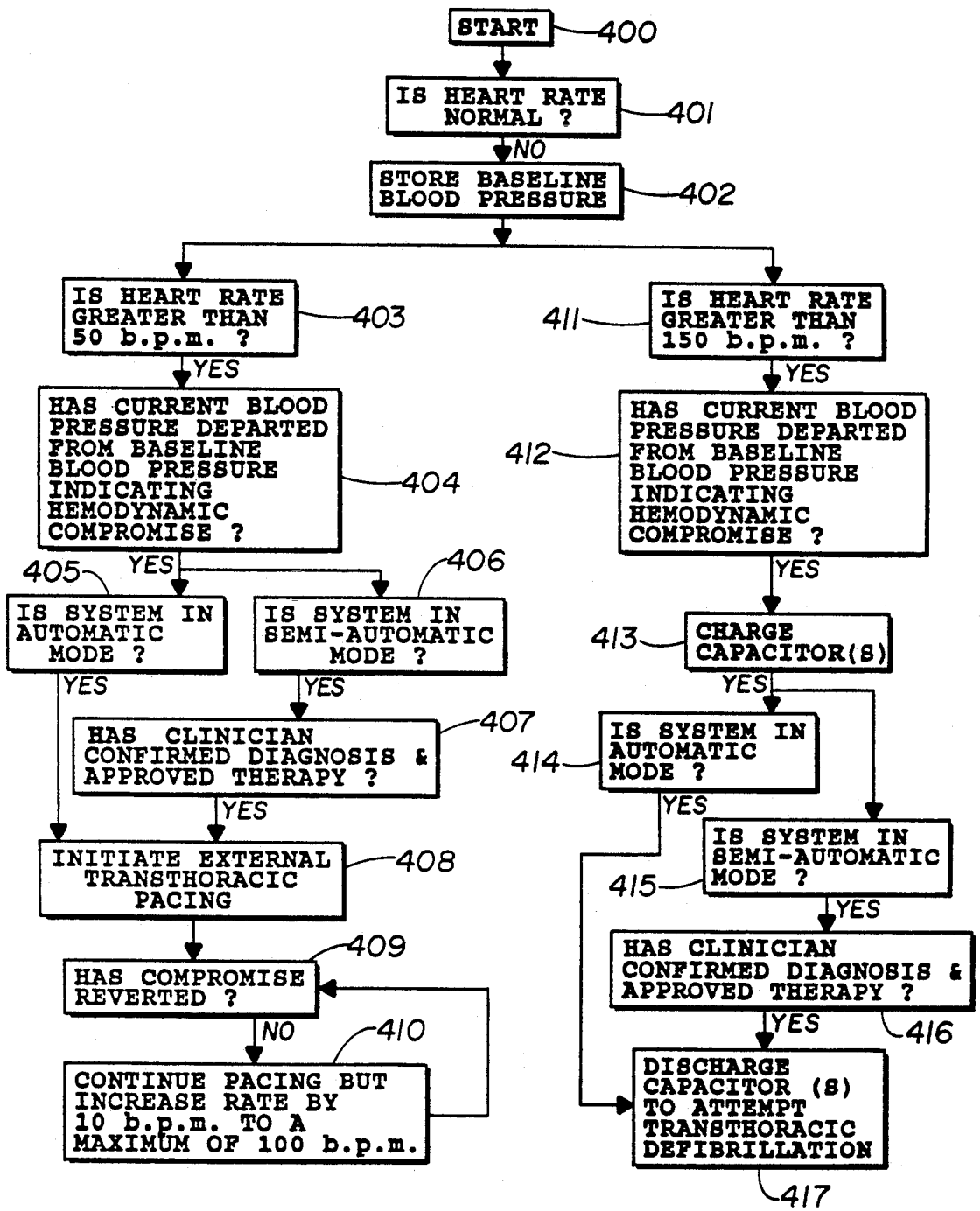
FIG. 4 constitutes a flowchart of steps which may be executed by the systems illustrated in FIGS. 1 and 2, in which a capacitor(s) is charged as a prelude to cardioverting/defibrillating in both the automatic and semiautomatic modes.
Figure 5A:
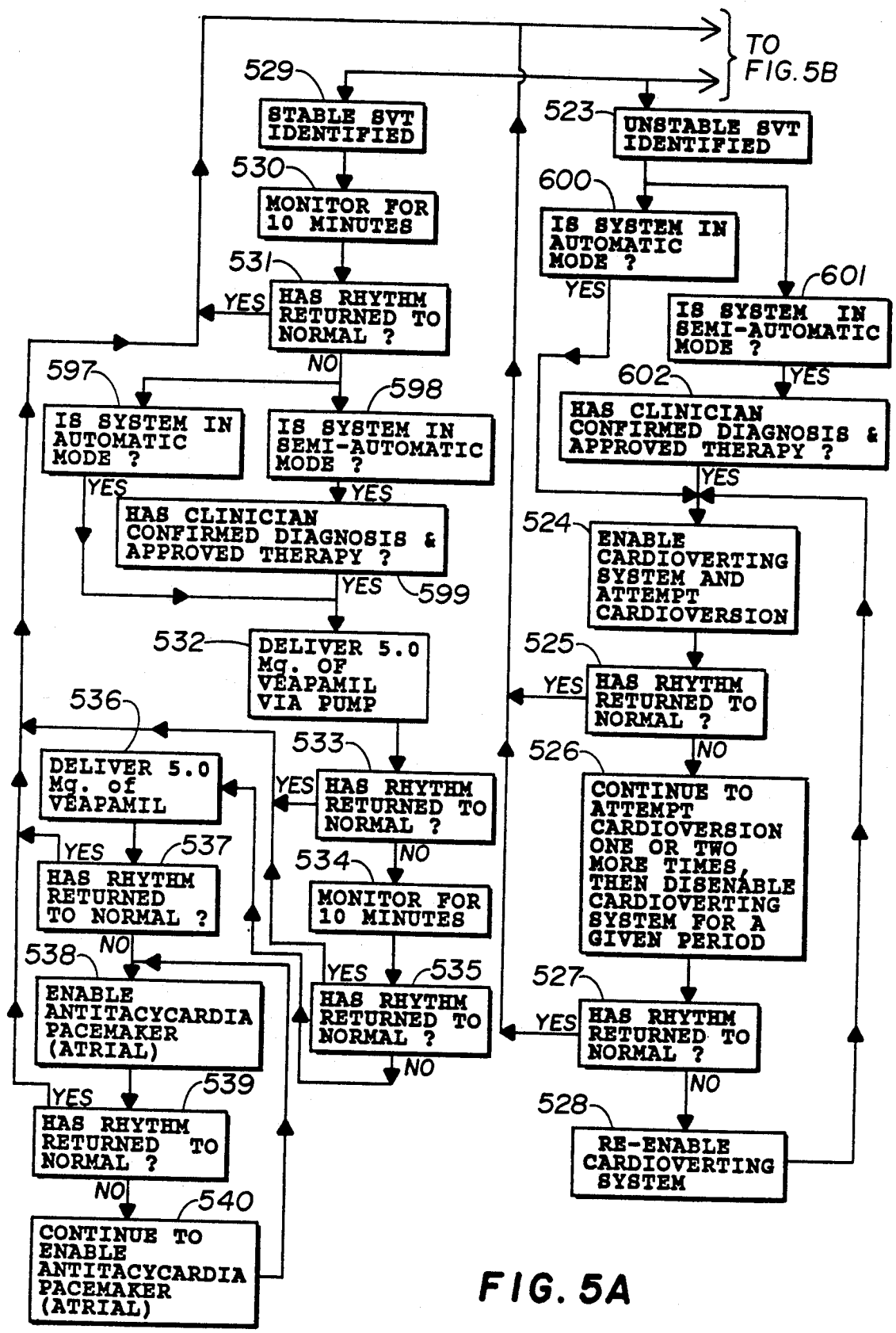
FIGS. 5A-5I, when taken together, constitute a flowchart of steps which may be executed by the systems illustrated in FIGS. 1 and 2.
Figure 5B:
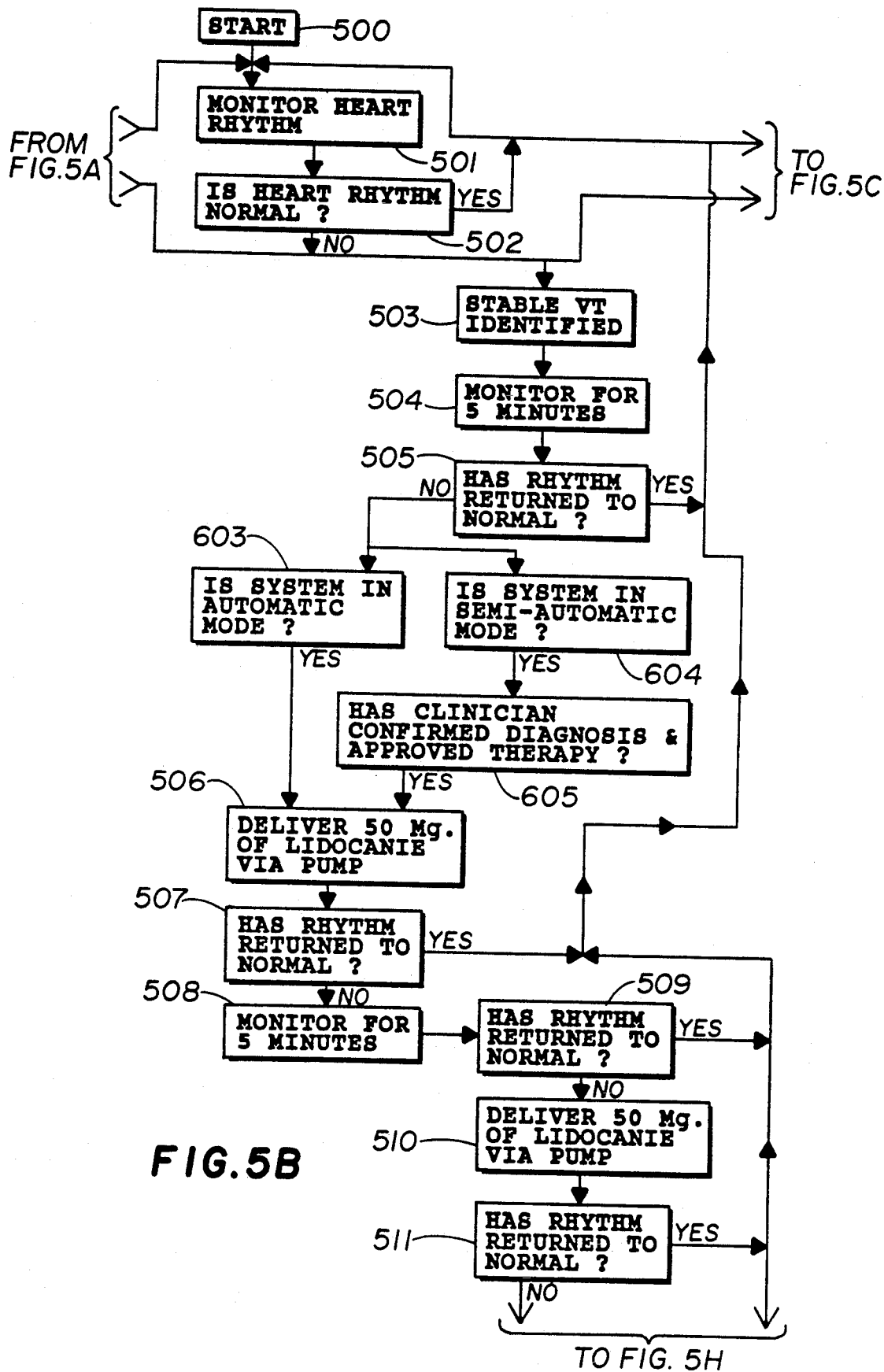
Figure 5C:
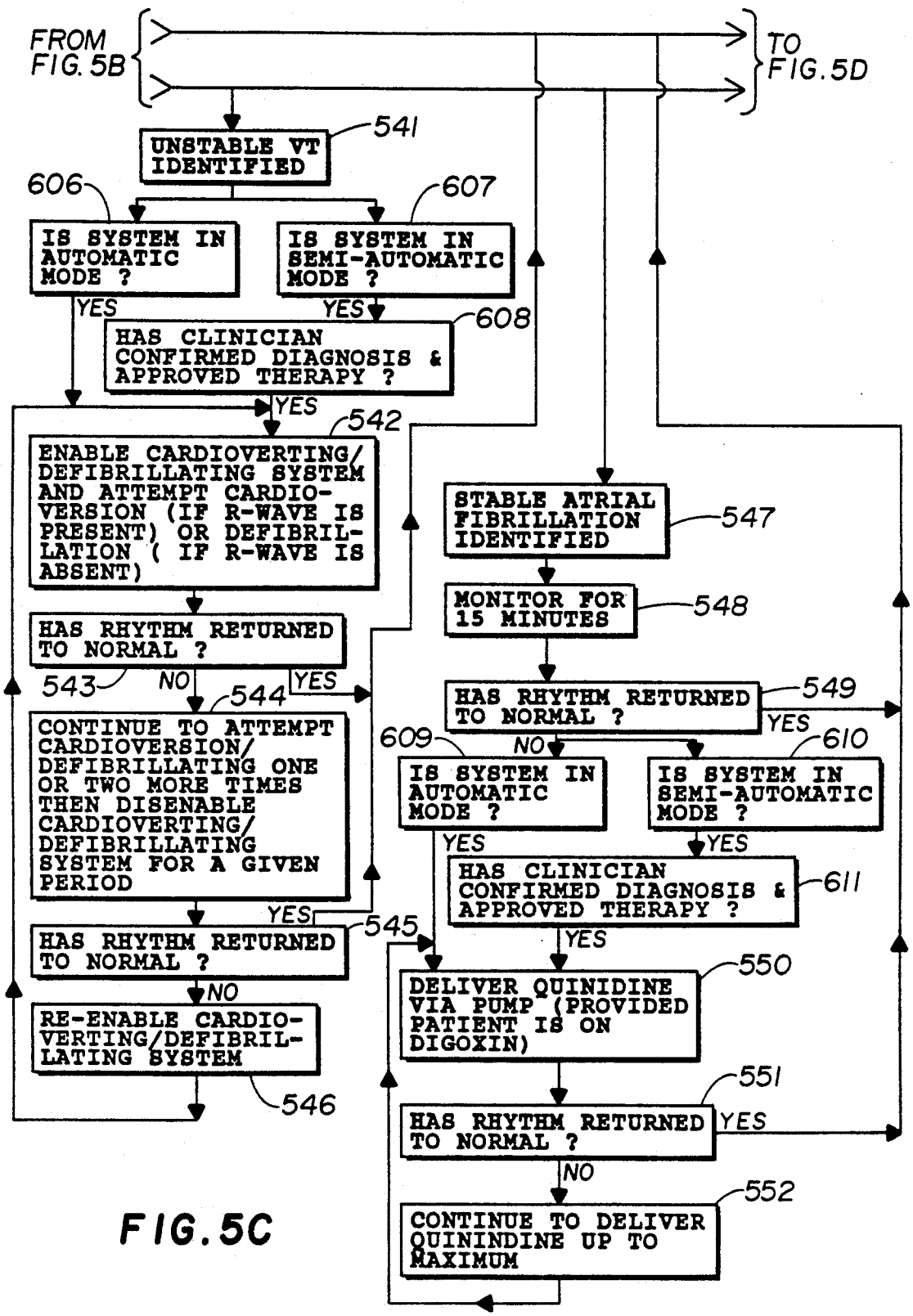
Figure 5D:
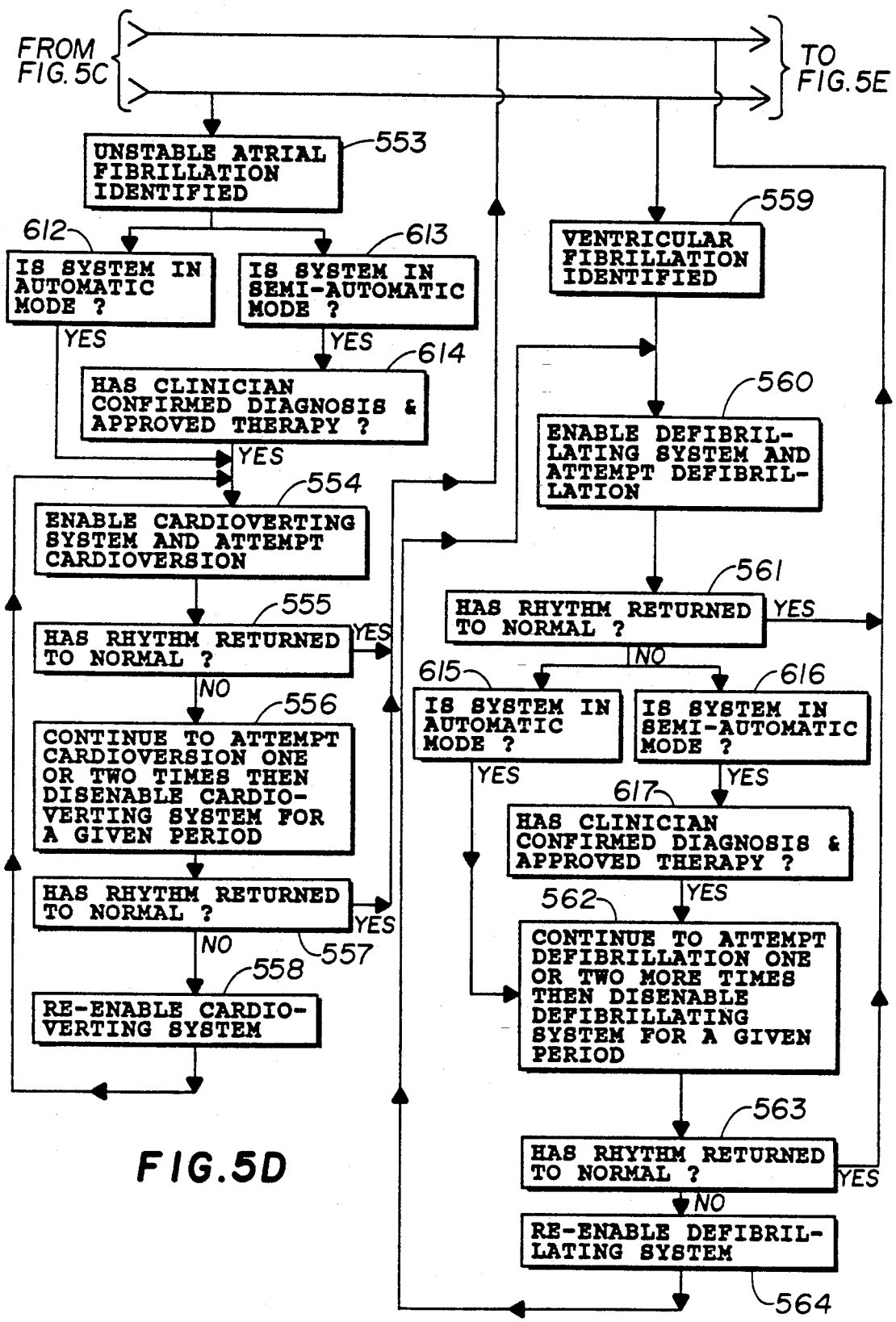
Figure 5E:
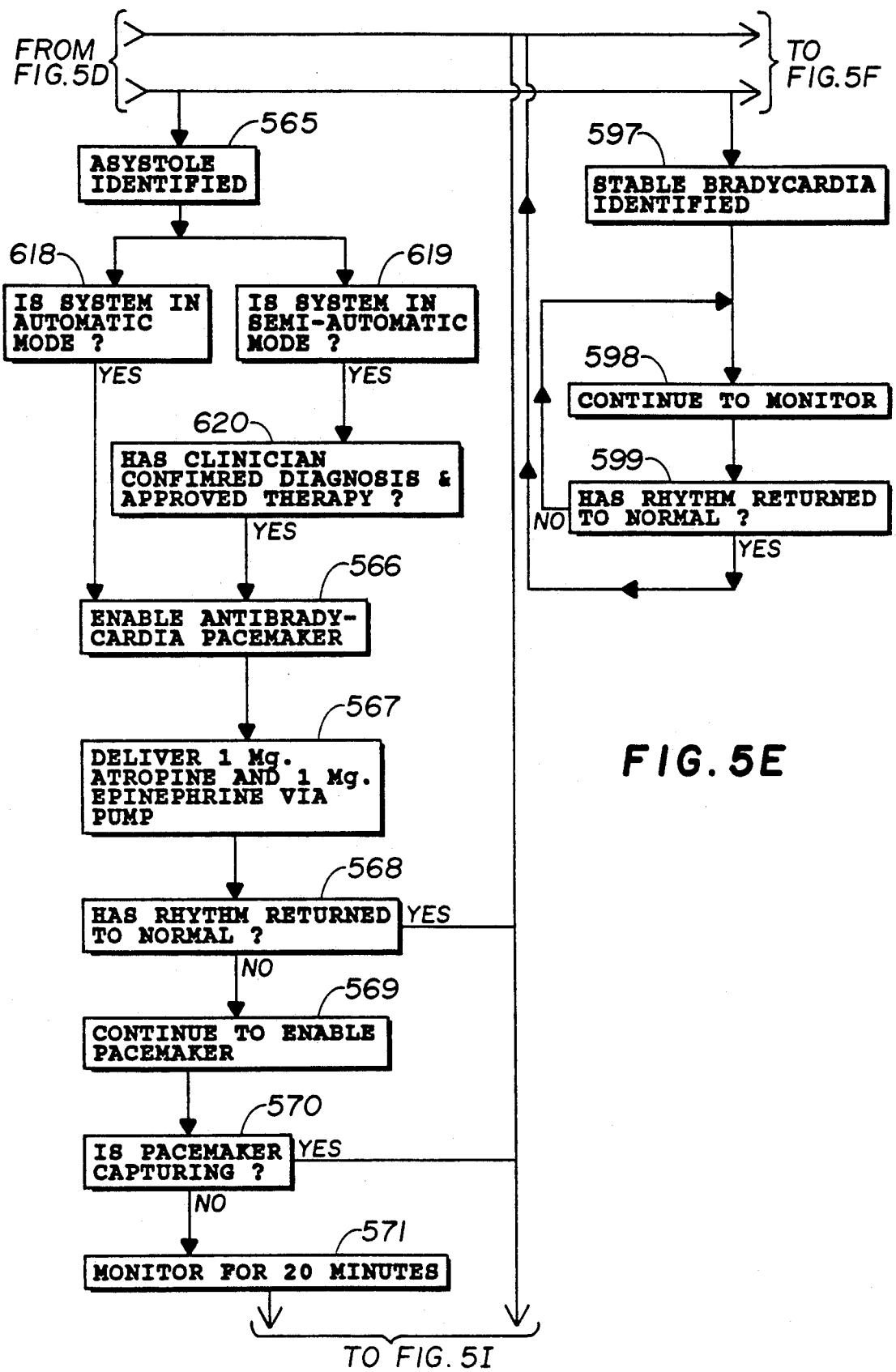
Figure 5F:
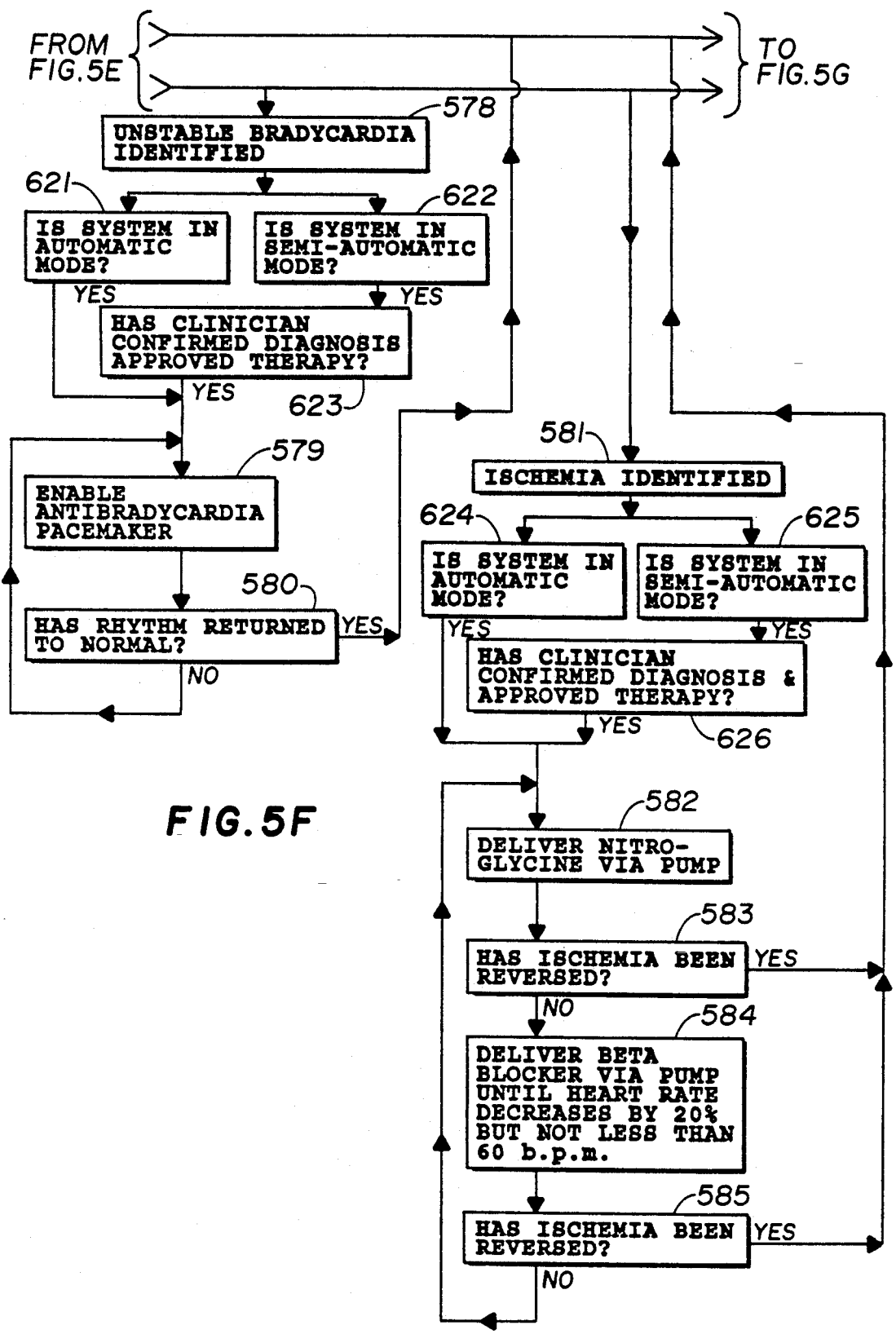
Figure 5G:
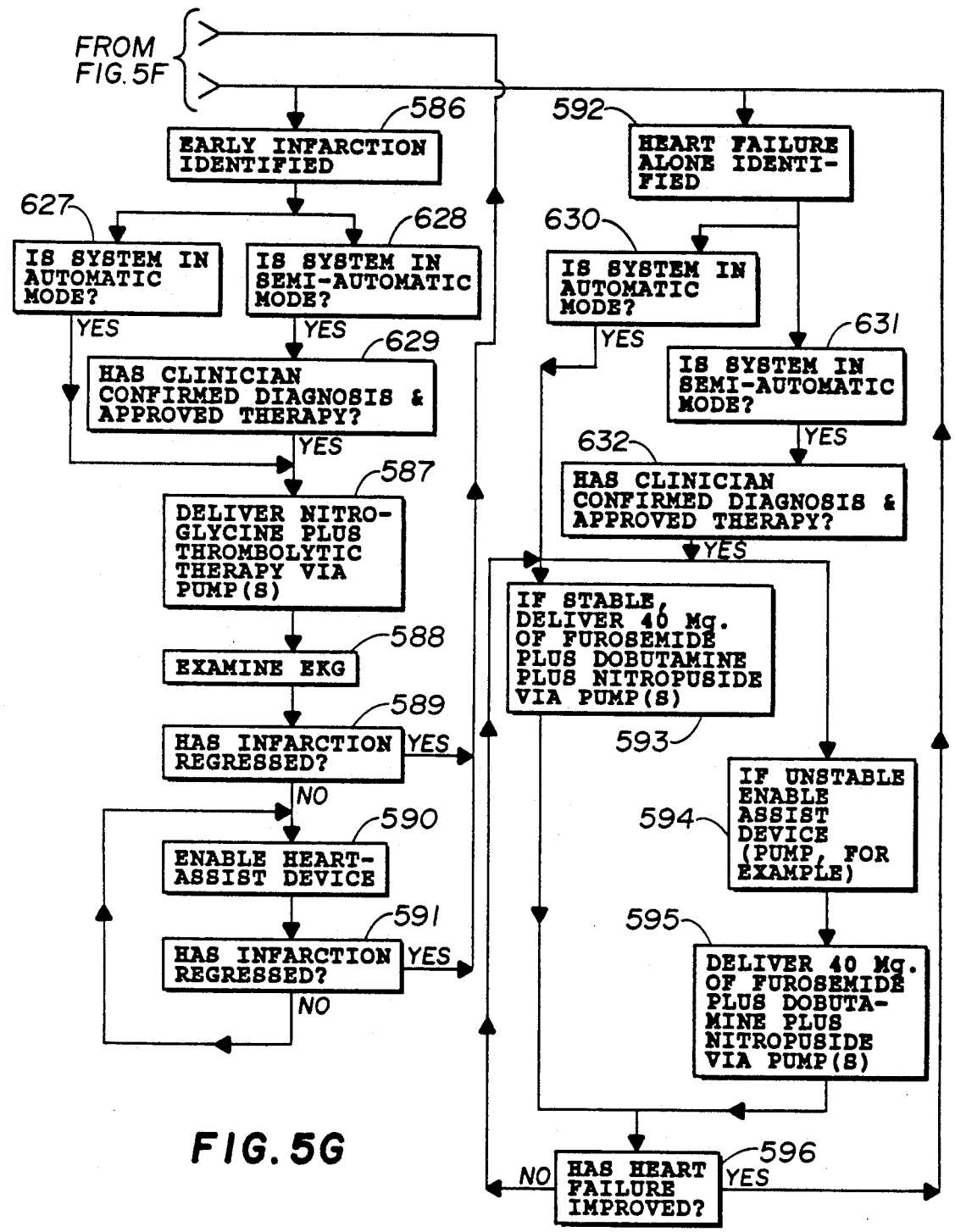
Figure 5H:
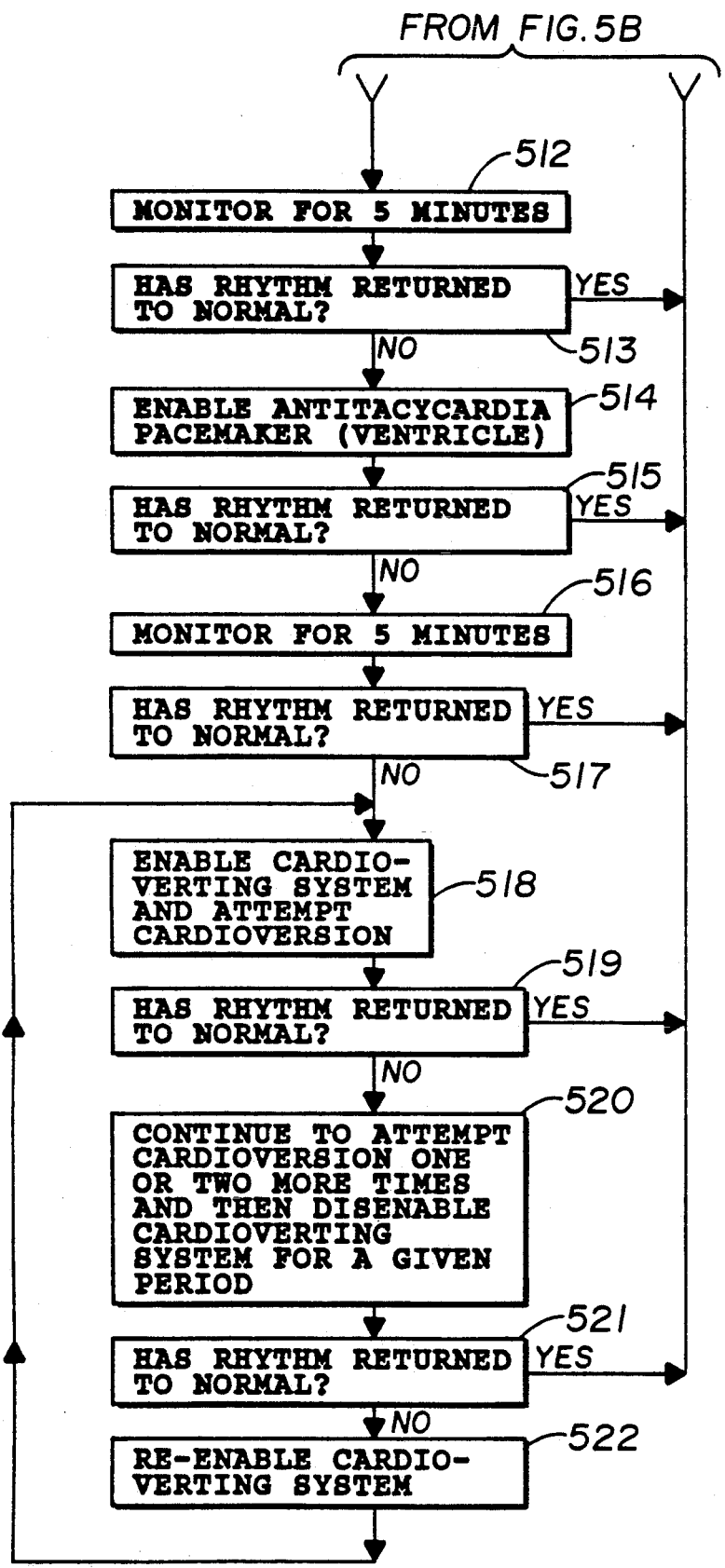
Figure 5I:
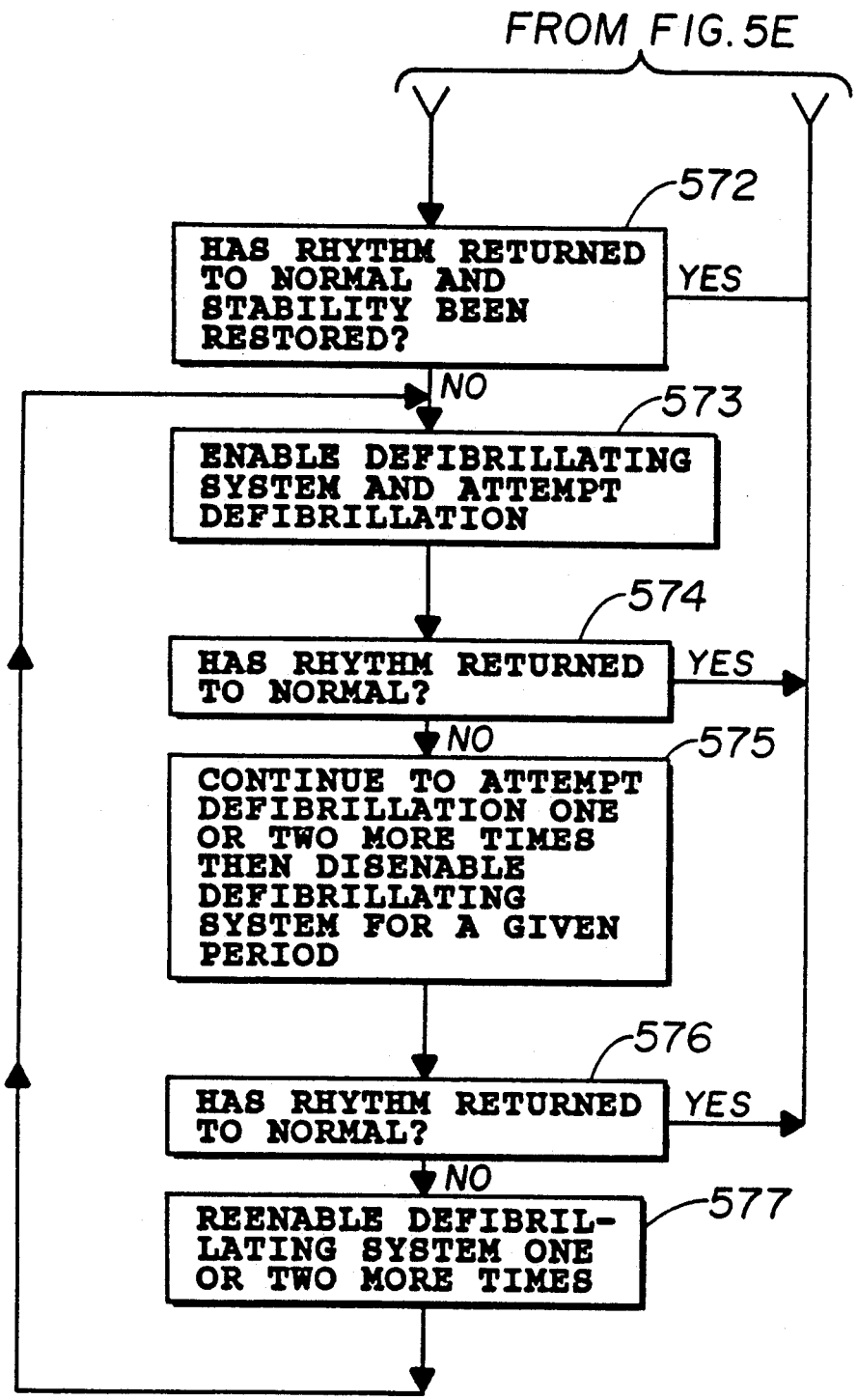
Figure 6:
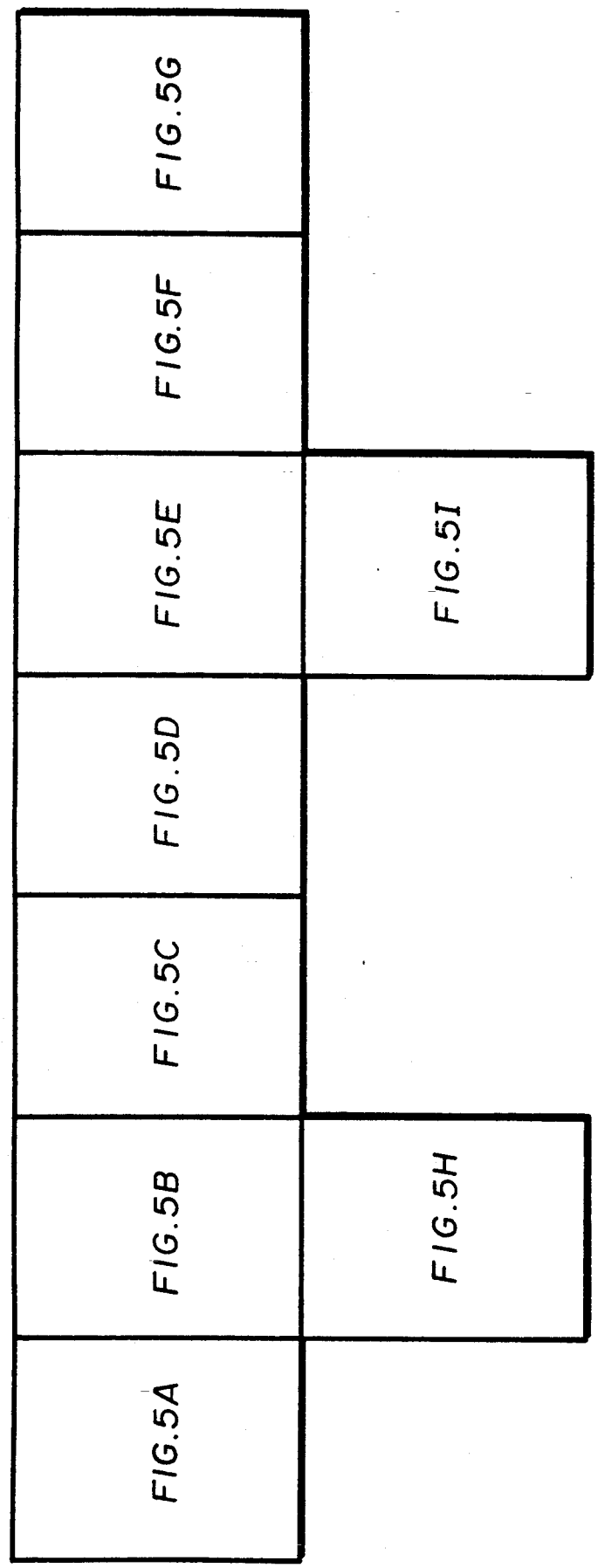
FIG. 6 is a diagrammatic showing of the placement of FIGS. 5A-5I in order to view these figures can be viewed as a whole.

The CPU 13, using programs stored in the ROM 21, determines if any of the malfunctions set out in FIG. 3, 4 and, in somewhat more detail, in FIGS. 5A–5I is present and produces control signals which are fed respectively to the antitachycardia pacemaker 14, to the antibradycardia pacemaker 15, to the cardioverter 16, to the defibrillator 17, to the respective drug delivery devices 18a–18d and to the heart-assist device (pump) 19. Each of the pacemakers 14 and 15 receive two possible pacing command signals from the CPU 13, one to effect production of an atrial pacing and the other to effect ventricular pacing. Thus, single or dual chamber pacing is possible when an effort is under way to treat tachycardia or bradycardia. The diagnostic and treatment routines which are carried out by the central processing unit 13, with its associated RAM 21 and ROM 22, are set out in blocks 300–316 of FIG. 3, in blocks 400–417 of FIG. 4 and 500–636 of FIGS. 5A–5I. As in the system illustrated in FIG. 1, the attending clinician or physician may elect, using the programmer 7, to allow the system to operate in its automatic mode or to operate in its semiautomatic mode. In the latter case, the CPU 13, which supplies a diagnostic output to the diagnostic display 9 so that the diagnostic conclusion can be viewed by the clinician or physician. The clinician or physician thus, if he wishes to proceed with providing heart-malfunction-corrective input(s) to the patient, simply presses the button 8 with signals the CPU 13 to enable one or another or pluralities of the devices 14–17, 18a, 18b, 18c, 18d or 19 in an attempt to correct the diagnosed heart malfunction.

It is to be understood that the foregoing detailed description and accompanying illustrations have been set out by way of example, not by way of limitation. The system may be adapted so that telephonic or radio telemetry could be used, allowing the clinician to be remote from the patient or patients other embodiments and variants are possible, without departing from the spirit and scope of the invention, its scope being defined in the appended claims.

I claim:

1. A multimode system for monitoring a patient and treating a malfunctioning heart of the patient selectively in automatic and semiautomatic modes, the system comprising means for deriving at least one electrical signal representative of electrical action of the heart and at least one physiological signal representative of a physiologic parameter of the patient, monitoring means for displaying the at least one electrical signal and the at least one physiologic signal, means for controlling delivery of at least one heart-malfunction-corrective input to the patient, means for inputting the at least one electrical signal and the at least one physiologic signal to said means for controlling delivery, output means responsive to output signals from said means for controlling delivery for providing the at least one heart-malfunction-corrective input to the patient, and means operable by a clinician or physician for enabling said means for providing the at least one heart-malfunction-corrective input to operate selectively in an automatic mode without action of the means operable by a clinician or physician and in a semiautomatic mode requiring confirmation by the clinician or physician, whereby at least one malfunction of the heart may be treated selectively in automatic and semiautomatic modes.

2. The multimode system of claim 1, wherein said means for controlling delivery comprises a central processing unit for controlling delivery of selected heart-malfunction-corrective inputs to the patient, wherein said means for inputting the at least one electrical signal and the at least one physiologic signal input same to said central processing unit, and wherein said output means respond to output signals from the central processing unit and provide under control of the central processing unit selectively in automatic and semiautomatic modes at least one heart-malfunction-corrective input to the patient from among a plurality of the heart-malfunction-corrective inputs, whereby malfunctions of the heart may be corrected.

3. The multimode system of claim 2, wherein the output means includes antitachycardia pacing means controlled by the central processing unit.

4. The multimode system of claim 2, wherein the output means includes antibradycardia pacing means controlled by the central processing unit.

5. The multimode system of claim 2, wherein the central processing unit is programmable.

6. The multimode system of claim 2, wherein the output means includes drug delivery means controlled by the central processing unit.

7. The multimode system of claim 2, wherein the output means includes a heart-assist device controlled by the central processing unit.

8. The multimode system of claim 2, wherein the output means includes drug delivery means, antitachycardia pacing means and antibradycardia pacing means and cardioverting/defibrillating means controlled by the central processing unit.

9. The multimode system of claim 2, wherein the output means includes antitachycardia pacing means and antibradycardia pacing means controlled by the central processing unit.

10. The multimode system of claim 2, wherein the output means further includes antibradycardia pacing means controlled by the central processing unit.

11. The multimode system of claim 2, wherein said output means includes cardioverting/defibrillating means.

12. The multimode system of claim 1, including means for monitoring heart rhythm to develop the at least one electrical signal, and means responsive to the at least one electrical signal and to the at least one physiologic signal for identifying stable supraventricular tachycardia.

13. The multimode system of claim 12, which includes means for supplying therapy to the patient whereby stable supraventricular tachycardia may be overcome.

14. The multimode system of claim 1, including means for monitoring heart rhythm to develop the at least one electrical signal, and means responsive to the at least one electrical signal and to the at least one physiologic signal for identifying unstable supraventricular tachycardia.

15. The multimode system of claim 14, which includes means for supplying therapy to the patient whereby unstable supraventricular tachycardia may be overcome.

16. The multimode system of claim 1, including means for monitoring heart rhythm to develop the at least one electrical signal, and means responsive to the at least one electrical signal and to the at least one physiologic signal for identifying stable ventricular tachycardia.

17. The multimode system of claim 16, which includes means for supplying therapy to the patient whereby stable ventricular tachycardia may be overcome.

18. The multimode system of claim 1, including means for monitoring heart rhythm to develop the at least one electrical signal, and means responsive to the at least one electrical signal and to the at least one physiologic signal for identifying unstable ventricular tachycardia.

19. The multimode system of claim 18, which includes means for supplying therapy to the patient whereby unstable ventricular tachycardia may be overcome.

20. The multimode system of claim 1, including means for monitoring heart rhythm to develop the at least one electrical signal, and means responsible to the at least one electrical signal for identifying rapid ventricular tachycardia and ventricular fibrillation.

21. The multimode system of claim 20, which includes means for supplying therapy to the patient whereby rapid ventricular tachycardia and ventricular fibrillation may be overcome.

22. The multimode system of claim 1, including means for monitoring heart rhythm to develop the at least one electrical signal, and means responsive to at least one electrical signal and to the at least one physiologic signal for identifying rapid ventricular fibrillation.

23. The multimode system of claim 22, which includes means for supplying therapy to the patient whereby rapid ventricular fibrillation may be overcome.

24. The multimode system of claim 1, including means for monitoring heart rhythm to develop the at least one electrical signal, and means responsive to the at least one electrical signal and to the at least one physiologic signal for identifying asystole.

25. The multimode system of claim 24, which includes means for supplying therapy to the patient whereby asystole may be overcome.

26. The multimode system of claim 1, including means for monitoring heart rhythm to develop the at least one electrical signal, and means responsive to the at least one electrical signal and to the at least one physiologic signal for identifying stable bradycardia.

27. The multimode system of claim 26, which includes means for supplying therapy to the patient whereby stable bradycardia may be overcome.

28. The multimode system of claim 1, including means for monitoring heart rhythm to develop the at least one electrical signal, and means responsive to the at least one electrical signal and to the at least one physiologic signal for identifying unstable bradycardia.

29. The multimode system of claim 28, which includes means for supplying therapy to the patient whereby unstable bradycardia may be overcome.

30. The multimode system of claim 1, including means for monitoring heart rhythm to develop the at least one electrical signal, and means responsive to the at least one electrical signal and to the at least one electrical signal and to the at least one physiologic signal for identifying ischemia.

31. The multimode system of claim 30, which includes means for supplying therapy to the patient whereby ischemia may be overcome.

32. The multimode system of claim 1, including means for monitoring heart rhythm to develop the at least one electrical signal, and means responsive to the at lest one electrical signal and to the at least one physiologic signal for identifying early infarction.

33. The multimode system of claim 32, which includes means for supplying therapy to the patient whereby early infarction may be overcome.

34. The multimode system of claim 1, including means for monitoring heart rhythm to develop the at least one electrical signal, and means responsive to the at least one electrical signal and to the at least one physiologic signal for identifying heart failure alone.

35. The multimode system of claim 34, which includes means for supplying therapy to the patient whereby heart failure alone may be overcome.

36. The multimode system of claim 1, including means coupled to said means for deriving at least one physiologic signal and responsive thereto for determining a change in a given physiologic parameter of at least a predetermined magnitude from a baseline for the parameter as represented by the physiologic signal.

37. The multimode system according to claim 1, including means coupled to said means for deriving at least one physiologic signal and responsive thereto over a period of given duration for establishing a varying baseline for a given physiologic parameter as represented by the physiologic signal, and means coupled to said means for deriving at least one physiologic signal and responsive thereto for determining current level of the parameter as represented by the physiologic signal over a period of predetermined duration which is shorter than the period of given duration.

38. The multimode system according to claim 1, including means for adjustably setting a baseline for a given physiologic parameter as represented by the physiologic signal.

39. A multimode system for monitoring a patient and for treating a malfunctioning heart of the patient selectively in automatic and semiautomatic modes by supplying cardioverting/defibrillating energy to the patient to overcome or avoid hemodynamic compromise, the system comprising means operable by a clinician or physician for providing a confirmation signal indicating a decision by the clinician or physician to apply cardioverting/defibrillating energy to the patient, computerized means having at least a first input and a second input, and at least one output, means for obtaining an electrical signal representative of electrical action of the patient's heart and for feeding that electrical signal to the first input of the computerized means, means for sensing at least one selected parameter of the patient's circulatory system to develop a physiologic signal representation thereof, means for feeding the physiologic signal to the second input, cardioverting/defibrillating means for delivering cardioverting/defibrillating energy to the patient, monitoring means for displaying the at least one electrical signal and the at least one physiologic signal, and means coupled to and responsive in its automatic mode to the output from the computerized means for triggering the cardioverting/defibrillating means to thereby provide automatically cardioverting/defibrillating energy to the patient's heart and responsive in its semiautomatic mode contemporaneously to the output from the computerized means and output from the confirmation signal source to thereby provide semiautomatically cardioverting/defibrillating energy to the patient's heart to avoid or overcome hemodynamic compromise of the patient.

40. The multimode system according to claim 39, including means within the computer means for establishing a baseline for the selected parameter of the patient to develop a baseline signal representation thereof, comparison means within said computerized -means for comparing the baseline signal on a short term basis with the physiological signal.

41. A multimode system treating a malfunctioning heart of a patient selectively in automatic and semiautomatic modes, the system comprising means for deriving at least one electrical signal representative of electrical action of the heart and at least one physiological signal representative of a physiologic parameter of the patient, means for controlling delivery of at least one heart-malfunction-corrective input to the patient, means for inputting the at least one electrical signal and the at least one physiologic signal to said means for controlling delivery, output means responsive to output signals from said means for controlling delivery for providing the at least one heart-malfunction-corrective input to the patient, and means operable by a clinician or physician for enabling said means for providing the at least one heart-malfunction-corrective input to operate selectively in an automatic mode without action of the means operable by a clinician or physician and in a semiautomatic mode requiring confirmation by the clinician or physician, whereby at least one malfunction of the heart may be treated selectively in automatic and semiautomatic modes.

42. A multimode system for treating a malfunctioning heart of the patient selectively in automatic and semiautomatic modes by supplying cardioverting/defibrillating energy to the patient to overcome or avoid hemodynamic compromise, the system comprising means operable by a clinician or physician for providing a confirmation signal indicating a decision by the clinician or physician to apply cardioverting/defibrillating energy to the patient, computerized means having at least a first input and a second input, and at least one output, means for obtaining an electrical signal representative of electrical action of the patient's heart and for feeding that electrical signal to the first input of the computerized means, means for sensing at least one selected parameter of the patient's circulatory system to develop a physiologic signal representation thereof, means for feeding the physiologic signal to the second input, cardioverting/defibrillating means for delivering cardioverting/defibrillating energy to the patient, and means coupled to and responsive in its automatic mode to the output from the computerized means for triggering the cardioverting/defibrillating means to thereby provide automatically cardioverting/defibrillating energy to the patient's heart and responsive in its semiautomatic mode contemporaneously to the output from the computerized means and output from the confirmation signal source to thereby provide semiautomatically cardioverting/defibrillating energy to the patient's heart to avoid or overcome hemodynamic compromise of the patient.

43. A multimode system for treating a malfunctioning heart of the patient selectively in automatic and semiautomatic modes by supplying at least one heart-malfunction-corrective input to the patient, the system comprising means operable by a clinician or physician for providing a confirmation signal indicating a decision by the clinician or physician to apply the at least one heart-malfunction-corrective input to the patient, computerized means having at least a first input and a second input, and at least one output, means for obtaining an electrical signal representative of electrical action of the patient's heart and for feeding that electrical signal to the first input of the computerized means, means for sensing at least one selected parameter of the patient's circulatory system to develop a physiologic signal representation thereof, means for feeding the physiologic signal to the second input, means for delivering at least one heart-malfunction-corrective input to the patient, and means coupled to and responsive in its automatic mode to the output from the computerized means for triggering the means for delivering at least one heart-malfunction-corrective input to thereby provide automatically corrective input to the patient and responsive in its semiautomatic mode contemporaneously to the output from the computerized means and output from the confirmation signal source to thereby provide semiautomatically corrective input to the patient to avoid or overcome at least one heart malfunction.

* * * * *